US010307053B2

(12) United States Patent
Fayolle

(10) Patent No.: US 10,307,053 B2
(45) Date of Patent: Jun. 4, 2019

(54) METHOD FOR CALIBRATING A HEAD-MOUNTED EYE TRACKING DEVICE

(71) Applicant: Essilor International, Charenton-le-Pont (FR)

(72) Inventor: Romain Fayolle, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/103,000

(22) PCT Filed: Dec. 16, 2014

(86) PCT No.: PCT/EP2014/078098
§ 371 (c)(1),
(2) Date: Jun. 9, 2016

(87) PCT Pub. No.: WO2015/091577
PCT Pub. Date: Jun. 25, 2015

(65) Prior Publication Data
US 2016/0302663 A1    Oct. 20, 2016

(30) Foreign Application Priority Data
Dec. 17, 2013  (EP) .................................... 13306750

(51) Int. Cl.
*A61B 3/14*     (2006.01)
*A61B 3/10*     (2006.01)
(Continued)

(52) U.S. Cl.
CPC ............ *A61B 3/113* (2013.01); *A61B 3/0091* (2013.01); *G02B 5/1866* (2013.01); *G02C 11/10* (2013.01);
(Continued)

(58) Field of Classification Search
CPC .......... A61B 3/103; A61B 3/14; A61B 3/113; A61B 3/152; A61B 3/1225; A61B 3/024;
(Continued)

(56) References Cited

U.S. PATENT DOCUMENTS 4,582,403 A     4/1986  Weinblatt
2004/0061831 A1* 4/2004  Aughey ................. A61B 3/113
                                              351/209

(Continued)

FOREIGN PATENT DOCUMENTS

EP    0845737 A2    6/1998
WO    0124688 A1    4/2001
WO    2010015962 A1  2/2010

OTHER PUBLICATIONS

International Search Report and Written Opinion dated Apr. 1, 2015; International PCT Application No. PCT/EP2014/078098.

*Primary Examiner* — Dawayne Pinkney
(74) *Attorney, Agent, or Firm* — Oblon, McClelland, Maier & Neustadt, L.L.P

(57) ABSTRACT

Method for calibrating a head-mounted eye tracking device, the method comprising: all acquisition step (S3), during which eye data relating to the position of the eye of the wearer are acquired by the eye tracking device while having the wearer of the head-mounted eye tracking device look in a direction of reference with regard to the spectacle lens mount, an association step (S4) during which the eye data acquired during the acquisition step are associated with the gaze direction corresponding to the direction of reference, a recording step (S5), during which the associated eye data and the gaze direction are recorded—wherein the head-mounted mounted eye tracking device comprises a spectacle frame in which ophthalmic lenses are mounted and the
(Continued)

Figure 2:
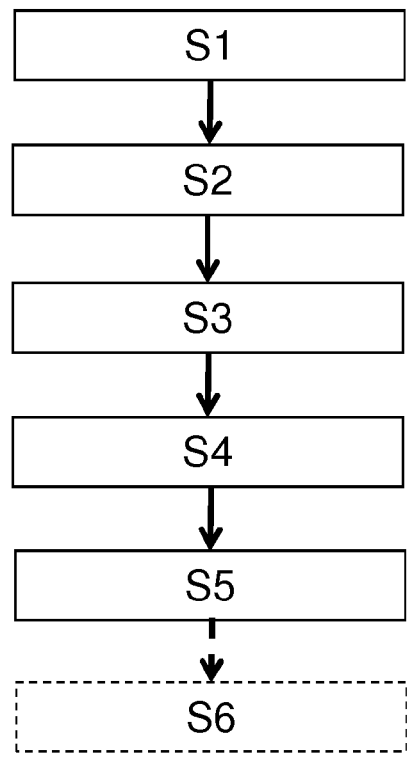

gazing direction corresponding to the direction of reference is determined based on the dioptric function of the ophthalmic lenses.

17 Claims, 2 Drawing Sheets

(51) Int. Cl.
    *A61B 3/02*     (2006.01)
    *A61B 3/00*     (2006.01)
    *A61B 3/113*     (2006.01)
    *G06F 3/01*     (2006.01)
    *G02B 5/18*     (2006.01)
    *G02C 11/00*     (2006.01)

(52) U.S. Cl.
    CPC ...... *G06F 3/013* (2013.01); *A61B 2560/0238* (2013.01)

(58) Field of Classification Search
CPC ......... A61B 3/032; A61B 3/04; A61B 3/1015; G02C 13/005
USPC ................ 351/204, 200, 205, 206, 208–210, 351/221–223, 233, 246
See application file for complete search history.

(56) References Cited

U.S. PATENT DOCUMENTS

| | | | |
|---|---|---|---|
| 2007/0132841 A1* | 6/2007 | MacDougall | A61B 3/113 348/78 |
| 2010/0053555 A1 | 3/2010 | Enriquez et al. | |
| 2011/0170065 A1* | 7/2011 | Sugio | A61B 5/0496 351/209 |
| 2013/0295994 A1* | 11/2013 | Guitteaud | F16M 13/00 455/556.1 |

* cited by examiner

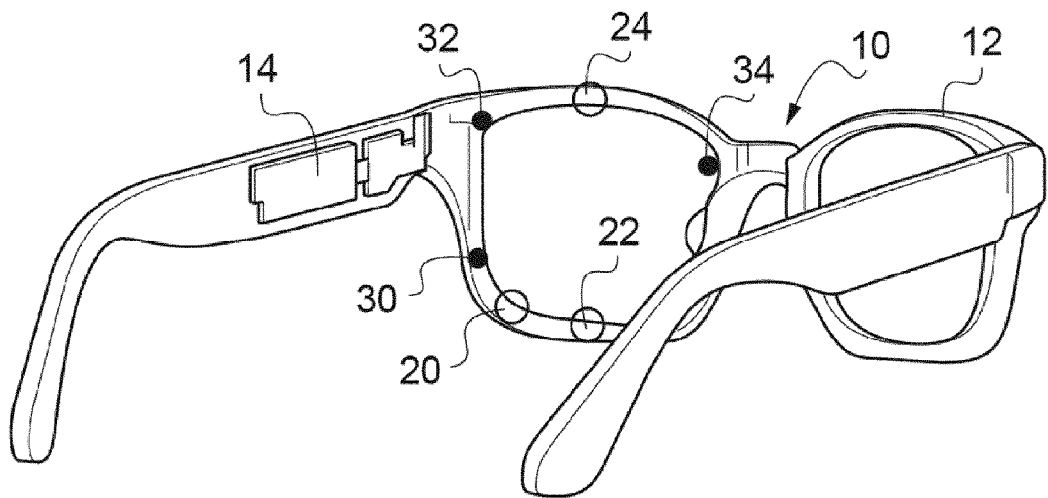
Fig. 1
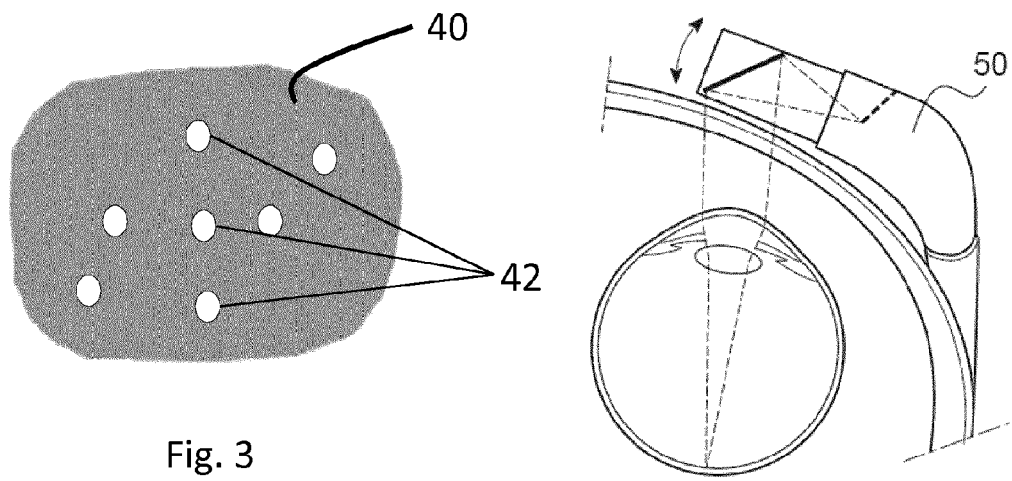
Fig. 3
Fig. 5

METHOD FOR CALIBRATING A HEAD-MOUNTED EYE TRACKING DEVICE

The invention relates to a method for calibrating a head-mounted eye tracking device and to a method for adjusting a head mounted eye tracking device having being calibrated by a method of calibration according to the invention.

The discussion of the background of the invention herein is included to explain the context of the invention. This is not to be taken as an admission that any of the material referred to was published, known or part of the common general knowledge at the priority date of any of the claims.

Eye tracking devices are more and more used in different technical fields. Head mounted eye tracking devices are usually invasive and uncomfortable for the wearer. Furthermore, existing eye tracking devices are usually heavy, in particular much heavier than a typical pair spectacle lenses. In some cases, special lenses are required (eg IR-reflective), and/or part of the field of view is obstructed by elements of the eye-tracking device.

Indeed, most of the eye tracking equipment favors tracking precision and robustness over the comfort of the wearer.

The comfort of the wearer is not considered as essential since most of the head-mounted eye tracking devices are intended to be used over a short period of time, typically the time to carry out some measurements on the wearer.

However, recent development in the field of ophthalmic lenses make it interesting to have the wearer carry an eye tracking system over long period of time, even all along day time.

Therefore the comfort of the eye tracking devices is more and more an issue. There has been attempts to adapt eye tracking devices to spectacle frames so as to increase the overall comfort of the eye tracking device however it appears that such adaptation provide poor results in terms of accuracy of the eye tracking.

One of the problems of using an eyetracker for a long period of time in a spectacle frame is that accuracy decreases over time, because the frame shifts over time.

One object of the invention is to provide a method for calibrating a head-mounted eye tracking device, in particular an eye tracking device mounted on a spectacle frame so that the eye tracking device does not present the drawbacks mentioned hereinabove.

To this end, the invention proposes a method for calibrating a head-mounted eye tracking device, the method comprising:
- an acquisition step during which eye data relating to the position of the eye of the wearer are acquired by the eye tracking device while having the wearer of the head-mounted eye tracking device look in a direction of reference,
- an association step during which the eye data acquired during the acquisition step are associated with the gaze direction corresponding to the direction of reference,
- a recording step during which the associated eye data and the gaze direction are recorded, wherein the head-mounted eye tracking device comprises a spectacle frame in which ophthalmic lenses are mounted and the gazing direction corresponding to the direction of reference is determined based on the dioptric function of the ophthalmic lenses.

Advantageously, the method according to the invention provides a calibration of the head-mounted device increasing the accuracy of the eye tracking device. The inventors have observed that even for eye tracking devices added on a conventional spectacle frame, the accuracy of the eye tracking device when using the method of calibration of the invention is increased. Therefore, when using the calibration method of the invention it appears possible to provide eye tracking devices mounted in a spectacle frame that are comfortable and provide accurate results in terms of eye tracking.

According to further embodiments which can be considered alone or in combination:
- the head-mounted eye tracking device comprises at least a visual reference element in the form of a microstructured pattern designed to diffract an incident light beam towards the wearer's eye under specific lightning conditions; and/or
- the method further comprises prior to the acquisition step:
  - a calibration support providing step, during which a calibration support comprising at least a visual reference element is provided to a wearer wearing the head mounted tracking device,
  - a placing step, during which the calibration support is placed between at least one eye of the wearer and the visual environment of the wearer in a known position relative to the wearer's eye and to the eye tracking device so as to define with the visual reference element a direction of reference; and/or
- the calibration support comprises a plurality of visual reference elements, and the association and recording steps are repeated for each visual reference elements; and/or
- the method further comprises after the last recording step a removing step during which the calibration support is removed; and/or
- the calibration support is opaque to light; and/or
- the at least one visual reference element is an optical opening in the calibration support, the optical opening being for example a hole, a portion of the calibration support conducting, emitting or transparent to light; and/or
- a switchable light source is attached to the at least one opening in the calibration support, and is configured to highlight the visual reference element (to catch the wearer's attention, to generate glints, and/or to control his pupil diameter) during the acquisition step; and/or
- the calibration support is transparent to visible light, and the at least one visual reference element is a microstructured pattern designed to diffract an incident light beam towards the wearer's eye; and/or
- the calibration support comprises an optical system generating a virtual image, the virtual display device been used to generate the at least one visual reference element; and/or
- the eye tracking device comprises a spectacle frame in which ophthalmic lenses are mounted, during the placing step the calibration support is placed on at least one of the surfaces of at least one of the ophthalmic lenses and the gazing direction corresponding to reference element is determined based on the dioptric function of the ophthalmic lenses; and/or
- the placing step calibration supports are placed on both of the optical lenses; and/ore
- the opening in the calibration support has a diameter greater than or equal to 0.6 mm and smaller than or equal to 1 mm; and/or
- the calibration support is a thin thermoformed layer; and/or
- the method further comprises an eye tracking position determining step during which the relative position of the eye tracking device relative to the face of the wearer when being worn by the wearer is determined; and/or the calibration support is initially a thin disk with prelocated reference elements, an can be edged to match with the spectacles' shape.

The invention also relates to a method for adjusting a head-mounted eye tracking device having being calibrated by a method of calibration according to the invention, the method comprising:

- a deviation determining step during which the deviation from an initial position of the relative position of the face of the wearer with respect to the eye tracking device is determined,
- an adjustment step during which the eye tracking function is adjusted based on the deviation determined during the deviation step, wherein the initial position corresponds to the relative position of the face of the wearer with respect to the eye tracking device during the calibration steps.

According to further embodiments which can be considered alone or in combination:

the deviation and adjustment steps are repeated regularly, for example every 30 seconds; and/or the deviation step, the distance between the eye and the eye tracking device and the relative position of the center of rotation of the eye with respect to the eye tracking device are determined; and/or the head mounted eye tracking device further comprises at least two light sources configured to illuminate at least one eye of the wearer, and wherein the distance between the eye and the tracking device is determined based on the geometric shape formed by the reflections of the light sources on the cornea of the eye of the wearer illuminated by the light sources, with regard to the pupil, in the field of view of an eye tracking camera.

According to a further aspect, the invention relates to a computer program product comprising one or more stored sequence of instruction that is accessible to a processor and which, when executed by the processor, causes the processor to carry out the steps of the methods according to the invention.

According to another aspect the invention relates to a program which makes a computer execute the method of the invention.

The invention also relates to a computer readable medium carrying one or more sequences of instructions of the computer program according to the invention.

The invention further relates to a computer-readable storage medium having a program recorded thereon; where the program makes the computer execute the method of the invention.

The invention relates to a device comprising a processor adapted to store one or more sequence of instructions and to carry out at least one of the steps of a method according to the invention.

Figure 4:
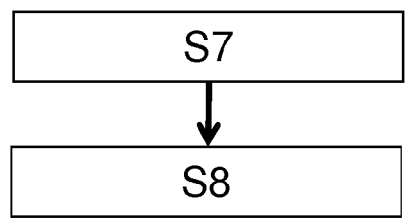

Non limiting embodiments of the invention will now be described with reference to the accompanying drawing wherein:

FIG. 1 is a schematic representation of an head mounted eye tracking device that may be calibrated according to the method of the invention, FIG. 2 is a flowchart representing the steps of a method for calibration a head mounted device according to the invention, FIG. 3 is a schematic representation of a calibration support, FIG. 4 is a flowchart representing the steps of an adjustment method according to the invention, and FIG. 5 is a schematic representation of a calibration support using virtual image generator.

Elements in the figures are illustrated for simplicity and clarity and have not necessarily been drawn to scale. For example, the dimensions of some of the elements in the figure may be exaggerated relative to other elements to help improve the understanding of the embodiments of the present invention.

FIG. 1 represents an example of head-mounted eye tracking device 10 mounted on a spectacle frame 12. Although the method of calibration according to the invention is not limited to such type of head-mounted devices, it appears to be particularly advantageous for eye tracking devices arranged in spectacle frames.

Indeed, the inventors have observed that the calibration method according to the invention increases the accuracy of head mounted eye tracking devices, in particular of eye tracking devices arranged in spectacle frames.

The eye tracking device 10 represented on FIG. 1 comprises a spectacle frame 12 with three cameras 20, 22, 24 directed at the left eye (not shown) of the wearer. The cameras 20, 22, 24 are arranged to be directed toward the head in order to track the locations of the eyes of the wearer and/or the structures of the eyes of the wearer, for example the pupils, eyelids, irises, glints, and/or other reference points in the region of the eye(s).

The cameras 20, 22, 24 may include charge-coupled device (CCD), complementary metal-oxide-semiconductor (CMOS), or other photodetectors that include an active area, e.g., including a rectangular or linear or other array of pixels, for capturing images and/or generating video signals representing the images. The active area of each of the cameras 20, 22, 24 may have any desired shape, e.g., a square or rectangular shape, circular, and the like. The surface of the active area of one or more cameras may also be curved, if desired, e.g., to compensate during image acquisition for the nearby three-dimensional curvature of the eye and surrounding structures being imaged.

The eye tracking device 10 further comprises three illumination sources 30, 32, 34 arranged to as to illuminate the left eye of the wearer when wearing the spectacle frame 12.

The three illumination sources 30, 32, 34 are fixed to the spectacle frame 12. In an exemplary embodiment, illumination sources 30, 32, 34 may include light-emitting diodes (LEDs), organic LEDs (OLEDs), laser diodes, or other devices that convert electrical energy into photons. Each illumination source 30, 32, 34 may be used to illuminate the eye to acquire images using any of the cameras 20, 22, 24 and/or to produce reference glints for measurement purposes to improve gaze-tracking accuracy. In an exemplary embodiment, each light source 30, 32, 34 may be configured for emitting a relatively narrow or wide bandwidth of the light, for example infrared light at one or more wavelengths between about 700-1000 nanometers. For example, AlGaAs LEDs provides an emission peak at 850 nm and are widely used and affordable, while commodity CMOS cameras used in mobile phones and webcams show a good sensibility at this wavelength.

The eye tracking device 10 further comprises a processing unit 14 arranged to receive the images collected by the cameras 20, 22, 24. The processing unit is arranged in one of the sides of the spectacle frame.

Although not represented, the eye tracking device further comprises a power source, for example a battery and/or other electronics. Advantageously, to distribute weight more evenly within the spectacle frame 12, the power source and/or other electronics may arranged in the side of the spectacle frame opposite to the one containing the processing unit 14.

Advantageously, such head mounted eye tracking device being included in a spectacle frame the wearer may use the eye tracking device over long periods without being hindered.

Although on FIG. 1 cameras and illumination sources have been represented only on the left side of the spectacle frame, the eye tracking device may very well comprise cameras and illumination sources and/or on the right side of the spectacle frame.

Advantageously, having cameras on both sides of the spectacle frame allows providing accurate information on the gazing direction and distance of the wearer.

For example, such eye tracking device can be used for long periods of time so as to determine accurately in everyday life conditions the visual behavior of the wearer.

Such eye tracking device may also be combined with active spectacle lenses. For example, the optical function of the optical lenses may be adapted using the gazing direction and distance of the wearer, or its history over a period of time.

In the sense of the invention, the optical function corresponds to a function providing for each gaze direction the effect of the optical lens on the light ray passing through the optical lens.

The optical function may comprise dioptric function, light absorption, polarizing capability, reinforcement of contrast capacity, etc. . . .

The dioptric function corresponds to the optical lens power (mean power, astigmatism etc . . . ) as a function of the gaze direction.

The method of calibration according to the invention is particularly adapted for the eye tracking devices mounted in a spectacle frame as illustrated on FIG. 1.

As an alternative, instead of using cameras and illumination source, any other eyetracking such as electroocculography or other method can be used for the tracking at least one of the eye.

According to a first embodiment of the invention illustrated on FIG. 2, the method for calibrating a head mounted eye tracking device comprises:
 a calibration support providing step S1,
 a placing step S2,
 an acquisition step S3,
 an association step S4, and
 a recording step S5.

During the calibration support providing step S1, a calibration support is provided to a wearer wearing the head mounted eye tracking device to be calibrated.

The calibration support comprises at least a visual reference element.

An example of calibration support is represented on FIG. 3. The calibration support 40 represented on FIG. 2 is opaque to light and comprises a plurality of optical openings 42 as visual reference elements. According to an embodiment of the invention, the optical openings have a diameter greater than or equal to 0.6 mm and smaller than or equal to 1 mm.

According to an embodiment of the invention, at least one switchable light source can be attached to at least one optical opening in the calibration support, and be configured to highlight the visual reference element so as to catch the wearer's attention, and/or to generate a reflection on the cornea ("glint"), and/or to control his pupil diameter.

According to a further embodiment of the invention, the calibration support may be a thin thermoformed layer, for example having a thickness greater than 25 μm and smaller than 1 mm. Such thin thermoformed layer is particularly advantageous when the eye tracking device comprises a spectacle frame in which ophthalmic lenses are mounted. Indeed, the calibration support may easily be placed on at least one of the surfaces of at least one of the ophthalmic lenses, for example both of the ophthalmic lenses. For example a calibration support is place on the front surfaces of each of the ophthalmic lenses mounted in the spectacle frame.

According to a further embodiment the calibration support may be transparent to visible light, and the at least one visual reference element is a microstructured pattern designed to diffract an incident light beam towards the wearer's eye. Such calibration support could for example be the optical lenses themselves. Indeed, the optical lenses mounted in the spectacle frame may comprise microstructured pattern either internal or engraved on one or both of the surfaces of the optical lens. Such microstructured pattern is arranged so as to be invisible for the wearer under common lightening condition and to appear to the wearer under specific lightening conditions, for example using a specific lightening angle. Advantageously, having the calibration support incorporated in the optical lenses allows implementing the calibration method according to the invention more easily without the use of an additional support.

According to a further embodiment, as shown in FIG. 5, the calibration support may be a virtual image display device 50, preferably allowing the wearer to see both the virtual image and the real world through it. The virtual image display device is able to display graphical images, and an electronic driving system (memory+processor) sends to the virtual display image the image to display.

Preferably it is able to display image in different viewing directions, and the visual reference element are generated successively for different direction using an image in a form of a dot or a small circle.

During the placing step S2, the calibration support is placed between at least one eye of the wearer and the visual environment of the wearer.

The calibration support is generally placed before the wearer's eye at a distance of a few centimeters from the center of rotation of the eye of the wearer, for example between 25 and 35 mm from the center of rotation of the eye of the wearer.

The position of the calibration support relative to the wearer eye is known. Typically, the position of the calibration support relative to the center of rotation of the eye of the wearer is known.

According to an embodiment of the invention, calibration supports may be placed between both eyes of the wearer and the visual environment of the wearer, for example calibration supports are placed over both optical lenses of the spectacle frame. According to such embodiment the position of the calibration support relative to both eyes of the wearer are known.

As well, the position of the calibration support relative to the spectacle frame is known, in particular the position of the calibration support relative to the eye tracking device is known.

Knowing the position of the placed calibration support relative to the wearer's eye and to the spectacle frame, or to the eye tracking device, one may define for the visual reference element of the calibration support a direction of reference. According to the embodiment in which the calibration support comprises a plurality of visual reference elements, each visual reference element can be associated with a direction of reference.

During the acquisition step S3 eye data relating to the position of the eye of the wearer are acquired by the eye tracking device while having the wearer of the head-mounted eye tracking device look in the direction of reference.

For example, during the acquisition step the wearer is required to look at the or at one of the visual references of the calibration support. While the wearer is looking at the or at one of the visual references images of the eyes of the wearer are recorded by the cameras 20, 22 and 24 illustrated in FIG. 1.

During the association step S4 the eye data acquired during the acquisition step S3 are associated with the gaze direction corresponding to the direction of reference. The eye data are representative of the position of the eye and can be the positions of the glints, the position of the pupils, the position of the irises, a voltage (when using electrooculography) or any physical quantity providing information about the position of the eye.

As indicated previously, the method of calibration according to the invention may be used for calibrating eye tracking devices comprises a spectacle frame in which ophthalmic lenses are mounted.

Typically during the placing step S2 the calibration support is placed on at least one of the surfaces of at least one of the ophthalmic lenses and during the association step the gazing direction corresponding to reference element is determined based on the dioptric function of the ophthalmic lenses.

During the recording step S5 the associated eye data and the gaze direction are recorded, for example in a memory comprised in one of the sides of the spectacle frame.

According to the embodiment of the invention where the calibration support comprises a plurality of visual reference elements, the association and recording steps are repeated for each visual reference elements.

As indicated in FIG. 2, the method according to the invention may comprise after the last recording step a removing step S6 during which the calibration support is removed.

The calibration according to the invention allows collecting eye data, for example images of the eye of the wearer, related to gazing directions. Such data may be used during the eye tracking to increase the accuracy of the eye tracking device.

The inventors have observed that considering the movement of the eye tracking device relative to the face of the wearer can increase even more the accuracy of the eye tracking device.

Therefore, according to an embodiment of the invention, the method of calibration further comprises an eye tracking position determining step during which the relative position of the eye tracking device relative to the face of the wearer when being worn by the wearer is determined. Preferably the eye tracking position determining step is implemented prior to the acquisition step.

The invention further relates to a method for adjusting a head mounted eye tracking device having being calibrated by a method of calibration according to the invention.

As illustrated on FIG. 4, the adjusting method comprising:
a deviation determining step S, and
an adjustment step S8.

During the deviation determining step S7, the deviation from its initial position of the relative position of the face of the wearer with respect to the eye tracking device is determined.

The initial position of the relative position of the face of the wearer with respect to the eye tracking device is preferably determined during the eye tracking position determining step of the calibration method according to the invention.

The relative position of the face of the wearer comprises the distance between the eye of the wearer and at least one reference point of the eye tracking device, for example the distance between the cornea apex of the wearer and at least one reference point of the eye tracking device.

The relative position of the face of the wearer may further comprise the relative position of the center of rotation of the eye with respect to at least one reference point of the eye tracking device.

Such distances are preferably determined for each eye of the wearer when the eye tracking device is arranged for tracking both eyes of the wearer.

As illustrated on FIG. 1, the head mounted eye tracking device may comprises at least two light sources configured to illuminate at least one eye of the wearer. The distance between the eye and the tracking device may be determined based on the shape formed by the reflections of the light sources on the cornea of the eye of the wearer illuminated by the light sources.

According to a first embodiment, several light sources can be mounted on the spectacle frame. Each of the light sources creates a specular reflexion ("glint") visible in the camera image. If the light sources are small enough, the glints can be considered as points. The eye surface being quasi-spherical in several sections (central portion or iris, sclera), the apparent distance between glints can be, with adequate care, directly related to the distance between the eye surface and the eyeglasses.

According to a further embodiment, structured lighting can be used to project light patterns on the eye (e.g: square(s), stripes, line gratings, . . . ), with known solid angles with regard to the eyeglasses. The analysis of the reflected pattern of structured light from the eye to the camera can also directly lead to the calculation of Vertex distance (or Vertex distance variations).

According to an embodiment that can be combined with the previous embodiments, the analysis of pupil or iris apparent shape recordings over a period of time can lead to the localization of the eye rotation center in the camera field of view. With adequate care, one can also compute Vertex distance from this type of recordings.

The deviation determined during the deviation determining step S7 is used to adjust the eye tracking function of the eye tracking device during the adjustment step S8.

According to an embodiment of the invention the deviation and adjustment steps are repeated regularly, for example every 30 seconds.

Advantageously, the adjustment method of the invention allows maintaining a high accuracy of the eye tracking device although the eye tracking device may move relatively to the face of the wearer. For example, when the eye tracking device is of the type represented on FIG. 1, the eye tracking device may move relative to the face of the wearer, for example slide on the nose of the wearer or even be repositioned by the wearer. The adjustment method according to the invention allows adjusting the eye tracking function based on such movements.

As an example of adjustment, if the deviation of the eye is measured to be N mm on the horizontal (resp. vertical) axis, and M mm in the longitudinal axis (Vertex distance variation) the eye data will be modified so that the eye gazing direction measured with the position of the pupil, or irises, or glint will be modified.

A simple solution for this adjustment consists in modifying directly the eye data in order to cancel the effect of movements between eyeglasses and face. In a basic example, if a translation of the glasses occurs along an axis perpendicular to the eye camera optical axis, one can simply "translate" the detected eye position in the camera field of vision with the corresponding distance, in order to keep using initial calibration data without altering eye-tracking accuracy.

More generally, the adjustment method according to the invention aims at determining the expected "impact point" of gaze on the lens surface according to the observed movements between the eyeglasses and the wearer's face. Then, knowing the impact point and incidence on the lens, the gaze direction can be calculated with minimal precision loss.

The deviation can be measured, as an alternative to the deviation of the glint positions, as a deviation of the position of the cantus of the eyes, or more generally any deviation of features of the face relative to the eye tracking device, for example position of the nose, eyebrown, spots on the skin. The deviation can be measured by the eye tracking device itself, or by any additional camera or contactless sensors (eg: ultrasonic or time-of-flight distance sensor, photodetector array, capacitive proximity sensors, . . . ) positioned on the eye tracking device.

The deviation of the distance between the eye tracking device and the eye can also be measured with the determination of the iris apparent size in the camera image. A modified size of the iris in the image means that a deviation occurred, and a smaller size means that the distance between the eye and the eye tracking device increased. A simple model can be used to determine the deviation, knowing the iris size (12 mm approximately) and the pixel angular size of the camera.

$$Dist_{EtoET} \times \tan(Npix \times PixSize) = IrisSize \text{ so } Dist_{EtoET} \times \tan(Npix \times PixSize) \text{ with}$$
$Dis_{EtoET}$=distance between Eye and Eyetracker $Npix$=size in pixels of the iris, measured on the image of the eye $PixSize$=pixel angular size, known from the optical system of the camera imaging the eye.

$IrisSize$=size of the Iris (12 mm)

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for calibrating a head-mounted eye tracking device, the method comprising:
   acquiring eye data relating to a position of an eye of a wearer using at least one camera arranged on a spectacle frame of the head-mounted eye tracking device while having the wearer of the head-mounted eye tracking device look in a direction of reference;
   associating the eye data acquired during the acquiring with a gaze direction corresponding to the direction of reference using a processor of the head-mounted eye tracking device;
   recording the associated eye data and the gaze direction in a memory of the head-mounted eye tracking device,
   providing a calibration support comprising at least a visual reference element to the wearer wearing the head-mounted eye tracking device; and
   placing the calibration support between at least one eye of the wearer and a visual environment of the wearer in a known position relative to the wearer's eye and to the head-mounted eye tracking device so as to define with the visual reference element the direction of reference,
   wherein the head-mounted eye tracking device comprises ophthalmic lenses mounted on the spectacle frame of the head-mounted eye tracking device, and the gazing direction corresponding to the direction of reference is determined based on a dioptric function of the ophthalmic lenses, and
   wherein, during the placing, the calibration support is placed on at least one surface of at least one of the ophthalmic lenses and the gazing direction corresponding to the visual reference element is determined based on the dioptric function of the ophthalmic lenses.

2. The method according to claim 1, wherein the acquiring, the associating, and the recording are repeated.

3. The method according to claim 1, wherein the acquiring, the associating, and the recording step are repeated with at least one of the wearer gazing in a different direction of reference and at a different gazing distance.

4. The method according to claim 1, wherein the head-mounted eye tracking device comprises at least a visual reference element in the form of a microstructured pattern designed to diffract an incident light beam towards the wearer's eye under specific lightning conditions.

5. The method according to claim 1, wherein the calibration support comprises a plurality of visual reference elements, and the associating and recording are repeated for each visual reference element.

6. The method according to claim 1, wherein the calibration support is transparent to visible light, and the at least one visual reference element is a microstructured pattern designed to diffract an incident light beam towards the wearer's eye.

7. The method according to claim 1, wherein the calibration support is opaque to light.

8. The method according to claim 1, wherein a switchable light source is attached to at least one opening in the calibration support, and is configured to highlight the visual reference element during the acquiring.

9. The method according to claim 1, wherein during the placing the calibration support is placed on at least one surface of at least one of the ophthalmic lenses and the gazing direction corresponding to the reference element is determined based on a dioptric function of the ophthalmic lenses.

10. The method according to claim 1, wherein the calibration support comprises an optical system generating a virtual image, and wherein a virtual display device is used to generate the at least one visual reference element.

11. The method according to claim 1, wherein the method further comprises determining an eye tracking position during which a relative position of the head-mounted eye tracking device relative to a face of the wearer when being worn by the wearer is determined.

12. The method according to claim 11, the method further comprising:
  determining a deviation from an initial position of the relative position of the face of the wearer with respect to the head-mounted eye tracking device; and
  adjusting an eye tracking function based on the deviation determined during the determining of the deviation,
  wherein the initial position corresponds to the relative position of the face of the wearer with respect to the head-mounted eye tracking device during calibration.

13. The method according to claim 12, wherein the determining of the deviation and the adjusting are repeated every 30 seconds.

14. The method according to claim 12, wherein during the determining of the deviation, a distance between the eye and the eye tracking device and the relative position of a center of rotation of the eye with respect to the head-mounted eye tracking device are determined.

15. The method according to claim 14, wherein the head-mounted eye tracking device further comprises at least two light sources configured to illuminate at least one eye of the wearer, and wherein the distance between the eye and the head-mounted eye tracking device is determined based on a shape formed by reflections of the light sources on a cornea of the eye of the wearer illuminated by the light sources.

16. A computer program product stored on a non-transitory computer readable medium comprising stored sequences of instructions that are accessible to a processor and which, when executed by the processor, causes the processor to carry out the following:
  acquiring eye data relating to a position of an eye of a wearer using at least one camera arranged on a spectacle frame of a head-mounted eye tracking device while having the wearer of the head-mounted eye tracking device look in a direction of reference;
  associating the eye data acquired during the associating with a gaze direction corresponding to the direction of reference using a processor of the head-mounted eye tracking device;
  recording the associated eye data and the gaze direction in a memory of the head-mounted eye tracking device;
  providing a calibration support comprising at least a visual reference element to the wearer wearing the head-mounted eye tracking device; and
  placing the calibration support between at least one eye of the wearer and a visual environment of the wearer in a known position relative to the wearer's eye and to the head-mounted eye tracking device so as to define with the visual reference element the direction of reference,
  wherein the at least one visual reference element is an optical opening in the calibration support, and
  wherein the head-mounted eye tracking device comprises ophthalmic lenses mounted on the spectacle frame of the head-mounted eye tracking device, and the gazing direction corresponding to the direction of reference is determined based on a dioptric function of the ophthalmic lenses wherein, during the placing, the calibration support is placed on at least one surface of at least one of the ophthalmic lenses and the gazing direction corresponding to the visual reference element is determined based on the dioptric function of the ophthalmic lenses.

17. The computer program product according to claim 16, wherein the stored sequences of instructions that are accessible to the processor and which, when executed by the processor, causes the processor to further carry out the following:
  determining a deviation from an initial position of a relative position of a face of the wearer with respect to the head-mounted eye tracking device; and
  adjusting an eye tracking function based on the deviation determined during the determining of the deviation,
  wherein the initial position corresponds to the relative position of the face of the wearer with respect to the head-mounted eye tracking device during calibration.

* * * * *